United States Patent [19]

Strömberg et al.

[11] Patent Number: 5,769,537
[45] Date of Patent: Jun. 23, 1998

[54] METHOD AND APPARATUS FOR HANDLING AND DOSING OF AN ADDITIVE WHILE COLLECTING A LIQUID

[75] Inventors: Lennart Strömberg; Per J. Olsson, both of Saltsjöbaden, Sweden

[73] Assignee: SBS Medical Projects AB, Stockholm, Sweden

[21] Appl. No.: 676,403

[22] PCT Filed: Feb. 1, 1995

[86] PCT No.: PCT/SE95/00094

§ 371 Date: Jul. 23, 1996

§ 102(e) Date: Jul. 23, 1996

[87] PCT Pub. No.: WO95/21014

PCT Pub. Date: Aug. 10, 1995

[30] Foreign Application Priority Data

Feb. 2, 1994 [SE] Sweden ................................ 9400334

[51] Int. Cl.⁶ .................................................... B01F 13/00
[52] U.S. Cl. ...................... 366/163.1; 366/342; 366/108; 366/348
[58] Field of Search .................................... 366/349, 342, 366/152.1, 150.1, 163.1, 182.1, 182.4, 219, 220, 348, 110, 154.2, 108

[56] References Cited

U.S. PATENT DOCUMENTS 2,701,708  2/1955  Keen ....................................... 366/219
3,063,683  11/1962  Westbrook .............................. 366/220

FOREIGN PATENT DOCUMENTS

1920474  11/1970  Germany ................................ 366/220
468157   2/1992   Sweden.
1459702  2/1989   U.S.S.R. ................................ 366/342

*Primary Examiner*—Tony G. Soohoo
*Attorney, Agent, or Firm*—Larson & Taylor

[57] ABSTRACT

A method and an apparatus for sucking up and transporting liquids of various kinds through a suction unit (D) to a mixing and defoaming unit (F). A liquid or a liquid/air/gas mixture is sucked up by a suction nozzle (17) at the end of a suction unit (D) and, concurrently therewith, a dosing unit (E) with an additive (20, 20') is sucked up, proportionally to the amount of sucked up liquid from the nozzle (17). The dosing agent (20) is supplied directly into the liquid, as soon as there is any liquid in the suction unit (D) whereby, and is controlled such that no dosing agent is supplied to the mixing and defoaming unit when only air is sucked up through the nozzle (17). The fluid and dosing agent is passed into the mixing and defoaming unit (F) and is subjected to a G-force via a flexible hose (27) which is clamped between two mounts (30, 31). The intermediate portion of the flexible hose is rotated by an eccentric carrier (32) to provide a centrifugal G-force. The mixed liquid is then collected in a container having a filter (36) to separate any foam formed during mixing and dispensed to bags.

13 Claims, 3 Drawing Sheets

METHOD AND APPARATUS FOR HANDLING AND DOSING OF AN ADDITIVE WHILE COLLECTING A LIQUID

GENERAL DESCRIPTION

The present invention generally relates to a method and an apparatus for collecting and/or transporting liquids of various types, without any admixture of air or gas thereinto, and for storing said liquid in a closed, air or gas free container or receptacle, or for direct introducing the liquid into another liquid system, and handling said liquid without any contact with a human hand, and without the risque of contaminating said liquid during the handling thereof, and preferably under sterile conditions.

The invention is useful for handling of many various kinds of liquids and for many various purposes, in particular for handling of liquids which may de ruined, oxidized, gelified etc. depending on the influence of air or another gas, for handling of liquids which tend to form foam or froth during the handling thereof, liquids containing non-desired or harmful particles or impurities, mixed liquids which tend to separate or to form layers etc. during or after the collection thereof.

The method and the apparatus can be used for instance for handling of food stuffs like milk, cream, oils, syrups, juices etc., for handling of liquids of various kinds which are corrosive or harmful to the environement, and during the handling of which it is important that the liquid does not get in contact with a human skin or is let out in the nature or is drained. The invention may for instance be used for handling of oils or mixed liquids which do no solve in each other, in handling of blood in connection to medical operations, for sucking up waste liquids of various types, etc.

The invention has been developped especially in connection to handling of blood, and in the following the invention will mainly be described in connection to such handling. This is, however, no restriction of the invention to said particular field of use.

There is always a short supply of blood and large amounts of blood are needed and used for blood transfusions, for instance in connection to surgical operations. Blood is a very expensive product both as concerns the costs for collecting same, and also as concerns the costs for testing and storing same. During blood transfutions there is also a risque of transfer of jaundice, HIV infection and other diseases.

During many surgical operations the patient looses large amounts of blood, sometimes up to several liters. Normally such blood gets wasted and it is necessary that the patient gets a corresponding amount of blood by means of transfusions from blood donors.

Attempts have been made to solve the problem of the lack of blood in various ways. For instance, there are methods for purifying blood which has partly coagulated in connection to sucking up blood from the operation wound, but such methods are expensive and time consuming and also result in an inferior product. In some cases also so called "autotransfusions" have been practiced, and this is made in that the patient is tapped on his own blood some weeks in advance of a planned surgical operation, whereupon said patient, upon need, receives his own blood during or after the operation. The method, however, requires a planning of the surgical operation and can not be utilized in case of emergency operations. Generally it is also necessary that the patient is, at least, at a relatively good health when the blood is tapped in advance of the operation, and it is necessary that an equipment for eventual purification, cataloguing and storing of the patient's blood is available. Therefore the method has been used very rarely.

The object of the invention, according to the last mentioned aspect, that is the handling of blood, therefore has been the idea of collecting as much as possible of the patient's own blood, which blood gets lost during a medical operation and to return such blood the the patient himself.

In this connection three different main problems appear:
when blood is sucked up from a wound surface it can not be avoided that large amounts of air are also sucked into the system, and this leads to a heavy foam or froth formation, and this, in combination with the contact of the blood with foreign materials and with the free air, contributes to an initiation of the mechanisms which lead to an activation of the coagulation system of the blood and changes of, or in, the cells of the blood;

when storing such blood in some type of storing units air or another gas which is present will dominate the content of the storing unit, and this makes it impossible to immeditely return the blood to the patient;

the collected material also may contain non-desired tissue fragments from the operation wound (clots, muscle fragments, fats, bone particles etc.) which also activate the enzyme system of the blood.

According to the invention the above mentioned problems may be solved by a method and an apparatus, in which the blood is collected in air-free bags, without any admixture of air, so that the blood can be used later on, or in which the collected blood, which is sucked up during the surgical operation is and which has bleeded from the patient's own blood vessel system or after a tissue injury, is by time returned to the patient himself, and/or which blood is returned to the patient during the surgical operation (autologuous transfusion).

This is made in that the blood which leaves during the surgical operation is continuously sucked up, and the sucked up blood/air/gas mixture is immediately given an additive of an anti-coagulant, for instance a citrate of an active type known per se, of a desinfectant or of any type of an otherwise blood-preserving substance or agent, controlled by differential pressures existing in the system. The blood/air/gas mixture, handled in a closed system, is thereafter brought to pass a defoaming apparatus, in which the blood foam is dissolved, and in which adequate amounts of citrate and/or other dosing additives can always be added, and a filter in which non-desired particles are separated off, whereupon the blood is finally collected in a collection bag, completely without any admixture of air into the blood system.

It is known in connection to collection of blood in bottles or flexible bags to add an anti-coagulant, for instance a citrate, and this has generally been made in that a predetermined amount of a citrate solution is, in advance, supplied in the blood bag, which amount of citrate is calculated according to the amount of blood that the bag is meant to contain, whereby the citrate mixes with the incoming blood. The amount of blood which is sucked up may, however, vary, and if a less amount of blood is tapped into the blood bag than what is calculated the content of citrate in the blood bag will be higher than calculated content. Further, not even under favourable conditions the citrate will become mixed with the blood at the walls of the foam bubbles, and as a consequence coagulation will appear in said foam bubble walls.

Therefore an adequate addition of citrate and a complete admixing of citrate with blood and blood foam ought to be made as quickly as possible after the blood has been sucked up.

The dosing of citrate and eventual other additives to the liquid, which is sucked up, in the last mentioned case blood, therefore should be made in close proximity of the place where the blood is sucked up, and preferably at a place upstream of the place where the liquid (the blood) enters the means for defoaming/mixing and filtering of the liquid (the blood).

According to the invention the dosing apparatus for adding of citrate and/or other substances or agents is formed so that it provides, in a simple way, a surprisingly accurate dosing which is proportional to the amount of liquid which is sucked up.

This is made in that the dosing apparatus and the nozzle for sucking up liquid are connected to sub-pressures of different levels, and whereby the pressure gradient between said two pressure levels is chosen such that no additive at all is supplied when there is no liquid in the suction nozzle or in a suction hose, or in a suction tube connected thereto.

There have been problems in the said apparatus:

both to foresee that the liquid which is sucked up meets the additive as soon as possible after having been sucked up, and also to provide a delayed passing of the sucked up liquid and of the added liquid, so that said liquids get an optimum time for being completely mixed with each other, and to foresee that the additive, e.g. the citrate, is effectively and quickly asmixed in the liquid which is bound to the foam, which foam is irrevocably formed when the liquid is sucked up, thereby forseeing that the part of the liquid which has created the walls of the foam bubbles is mixed with the additive, and also to provide the most effective dissolving as possible of the foam, and a removing of the air part of the foam.

According to the invention the above mentioned problems can be effectively solved in that the sucked up liquid, as soon as possible after having been sucked up, is primarily mixed with the additive, and that the liquid with the additive, at the same time as the mixing takes place or immediately following the mixing thereof, is subjected to a centripetal force, in the following referred to as a G-force, of such magnitude that the air bubbles of the foam crack, that the air leaves, and that the liquid mixture is transferred to a collection bag via a collection container.

The G-force is preferably provided in that the sucked up liquid together with the additive is subjected to a rotary movement in some type of tube or container, which movement creates a G-force of desired strength. In handling of blood said G-force may be allowed to reach 2.500 G at a maximum.

Further characteristics of the invention and advantages thereof will be evident from the following detailed description of a couple of embodiments of the invention, which are shown in the accompanying drawings.

BRIEF DESCRIPTION OF THE DRAWINGS

In the drawings FIG. 1 diagrammatically, and in a simple design, shows an apparatus for executing the method according to the invention for sucking up liquid.

DETAILED DESCRIPTION OF THE INVENTION

The apparatus shown in FIG. 1 operates with a predetermined pressure gradient, namely a main sub-pressure P3 (suction) acting on certain parts of the apparatus, a certain higher pressure P2 (relatively less suction action) acting on other parts of the apparatus as will be explained in the following, and a third, still higher presure P1 which can be a constant external pressure, for instance atmospheric pressure, and at which the liquid or the liquid/air/gas mixture is being sucked up.

The apparatus comprises six main parts which are connected to form an integral unit. The part are the following:

A. a suction system having means for creating a sub-pressure of two different pressure levels, for instance a source of suction for creating a sub-pressure having a low level (P3) and a higher pressure level (P2), set by a choke valve B with a manometer C or another pressure indicator, and which suction system is connected to the various parts of the apparatus by means of a tube or hose system arranged for sucking up liquid under a still higher pressure (P1);

D. a suction means for sucking up liquid at atmospheric pressure or at another constant pressure P1;

E. a unit for dosing any type of one or more agents to be admixed to the liquid, for instance an antioxidant, an anticoagulant etc. which is under the pressure P3;

F. a mixing and defoaming unit which is connected to the suction means D and which is under the pressure P2;

G. a recipient in which the collected liquid with the added dosing agent is received, which is under the pressure P2, and which is formed with a bottom valve H for draining the liquid;

I. a packing unit for taking care of the filtered and de-aerated liquid and comprising one or more collection containers which are connected to the recipient G and is/are under the pressure P3.

Suction System A

Figure 1:
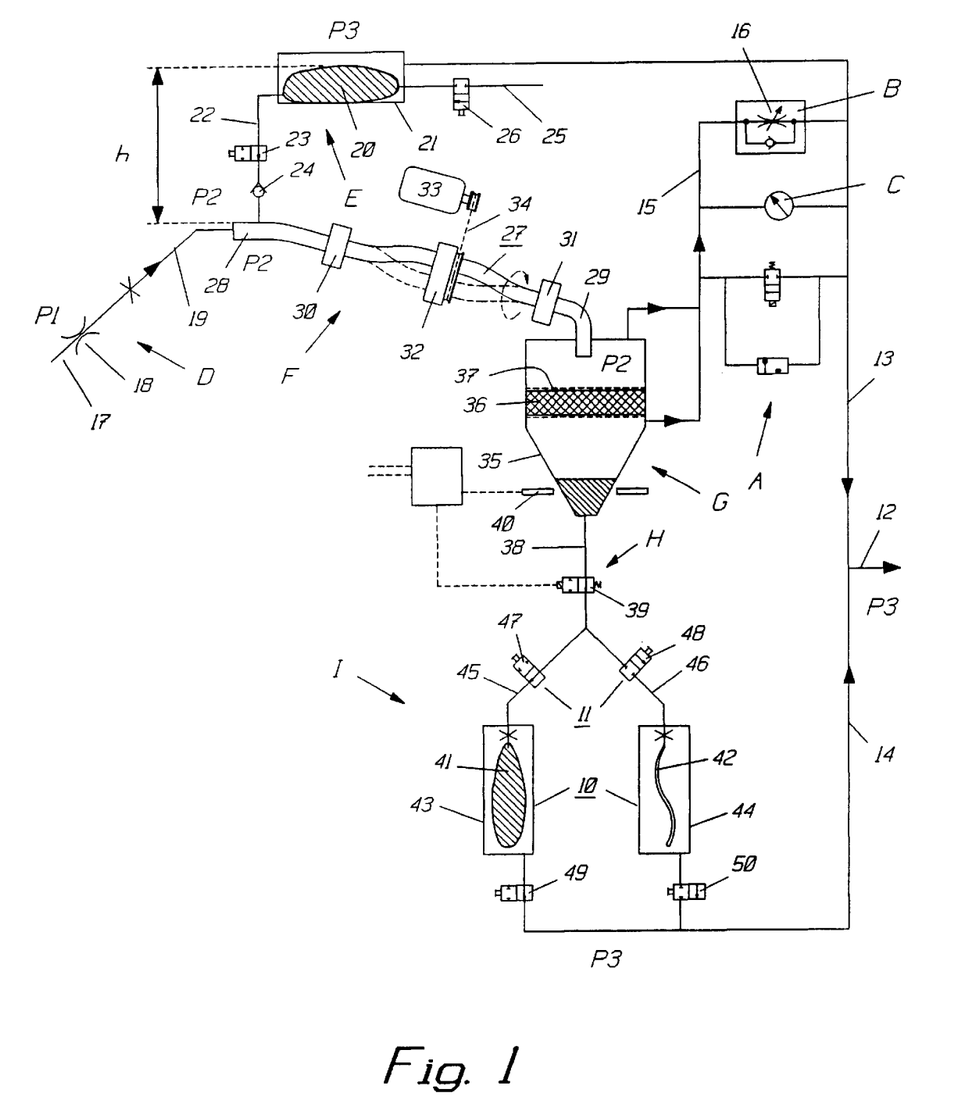

In the apparatus shown in FIG. 1 the suction system A comprises a suction connection 12 in the form of a tube or a hose which is connected to a suitable source of sub-pressure P3 (not shown) which can be any type of conventional or available source of sub-pressure, or which can be an air ejector pump or a similar means. The conduit from the suction connection 12 is connected to the dosing unit E over a first branch conduit 13, to a part of the packing unit I over a second branch conduit 14 and to the deaeration recipient G over a third branch conduit 15 and over the choke valve B, which is formed with some type of control means 16 and which may reduce the subpressure in said branch conduit and thereby in the recipient G to a predetermined extent, so that pressure P2 is slightly higher (less suction action) in the recipient G than in those parts of the apparatus which are under the pressure P3.

For making it possible to read the pressure gradient P2–P3 a manometer C or any other pressure indicator can be connected between the conduits 13 and 15 having the pressures P3 and P2 respectively.

The pressure gradient P2–P3 is controlled by setting 16 of the choke valve B, and said pressure gradient is set so that no dosing agent is supplied from the dosing unit E in case only air is introduced through the suction means D.

It is obvious to the expert that the two different subpressures P3 and P2 respectively may alternatively be received from two external sources of sub-pressure having said two pressure levels, whereby the choke valve B is omitted and the pressure P2 of the higher pressure level is supplied directly to the conduit 15 leading to the deaeration recipient G.

Suction Means D

The suction means D comprises a suction nozzle 17 of any known type suited for sucking up a liquid present in the open air or in any other type of gas or gas mixture. The nozzle 17 is connected to the the collection recipient G over a suction conduit 19 and over the mixing and defoaming unit F. The suction nozzle 17 operates with the pressure P2.

Dosing Unit E—the "inner" System

The dosing system shown in FIG. 1 is in the following referred to as the "inner" system considering the fact that the container bag containing the dosing agent is enclosed in a stiff casing which is under the pressure P3 which balances the supply of dosing agent.

Figure 5:
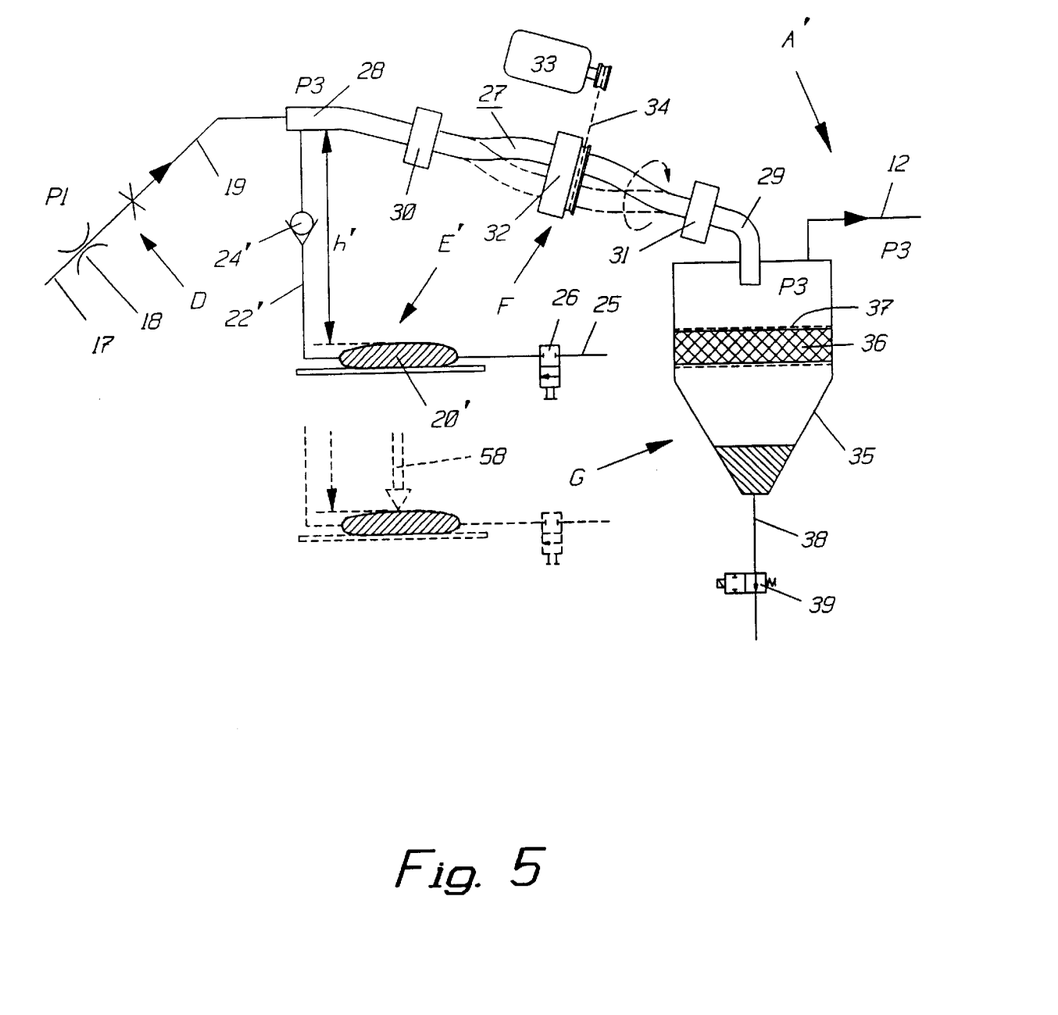
FIG. 5 shows an alternative embodiment of the means for providing a proportional supply of an additive to the liquid which has been sucked up in the same type of apparatus as that of FIG. 1.

At a place between the suction means D and the mixing an defoaming unit F there is a dosing unit E, or several dosing units for one or more dosing agents connected parallelly to each other. The dosing unit may be formed as an "inner" dosing system, which is shown in FIG. 1, or as an "outer" dosing system which is shown in FIG. 5.

In the apparatus shown in FIG. 1 the dosing unit comprises a flexible container 20 for the dosing agent, which is mounted on a higher level than that of the mixing and defoaming unit F, and which is enclosed in a stiff casing 21 which over the conduit 13 is connected to the pressure P3. The dosing container 20 is connected to the inlet of the mixing and defoaming unit F over a connection conduit 22 having a stop valve 23 and a non-return valve 24. The container 20 can be filled over a conduit 25 having a stop valve 26.

The pressure P3 in the casing 21 containing the dosing agent container 20 is less than the pressure P2 at the inlet of the mixing unit F in which the connection conduit 22 opens, and this creates a suction force corresponding to the pressure gradient P2-P3 acting on the liquid column having the height H from the container 20 to the inlet of the conduit 22 at the feeding end of the mixing unit F. Said suction force prevents dosing agent from flowing from the bag 20 into the mixing unit F until the pressure gradient P2–P3 is decreased, and this happens when the viscosity or the flow resistance increases in the medium introduced through suction nozzle 17 and the suction hose 19. Not until this situation appears dosing agent can flow down through the connection conduit 22 depending of the attraction of gravity. The mixing of dosing agent with the sucked up liquid is made in the mixing unit F. The amount of dosing agent which is supplied to the sucked up liquid is substantially proportional to the amount of liquid which is introduced through the suction nozzle.

In case the apparatus is used for collecting blood the dosing agent may for instance be a citrate solution which, as known by the expert in the field, is intended to bind the ionized calcium of the blood thereby preventing a coagulation of the blood. The dosing agent also may contain a disinfectant. It is also possible to provided two or more dosing apparatus parallelly to each other and arranged to dose both a citrate solution and a disinfectant and possibly still further agents. The additive may be a liquid, a gel, a powder etc. provided said agent can be brought to flow into the mixing unit F and can be mixed with the liquid which is sucked up. The additive also may be any agent or a mixture of agents having an active and diluting action on the liquid which is sucked up, or which is adapted to facilitate the solving of the foam, or which has another function.

The dosing agent also can be used for many other purposes, for instance for vitaminizing of liquid food stuffs, for adding emulsifiers to oil/water mixtures and for many other purposes.

Mixing and Defoaming Unit F

The mixnig and defoaming unit F is intended to provide a quick and effective admixing of a dosing agent into the liquid which is sucked up through the nozzle 17, even in case part of the liquid has formed a foam body emanating from the amount of air which is irrevocably introduced through the suction nozzle 17 together with the liquid. The unit F also is intended, at the same time, to provided a decomposition of the foam and a separation of air. The mixing and defoaming unit F is formed as a kind of apparatus which centrifuges the liquid and the foam thereby providing the effective admixing of the dosing agentwith the liquied and the defoaming of the liquid.

In the illustrated case the centrifugation apparatus comprises a flexible hose 27 which with the two ends 28, 29 thereof is kept still standing by two hose holding means 30, 31, and which with an intermediate hose part, extends through an eccentric carrier 32, which in the illustrated case, as one out of many possible examples, is rotated by a motor 33 over a drive belt 34. The inlet end 28 of the mixing hose 27 forms a receiver both for the liquid entering through the suction hose 19 and also for the dosing agent entering through the connection conduit 22. The outlet end 29 of the mixing hose 27 leads to the collection recipient or collection canister G. The mixing unit F preferably can be mounted slightly inclined in the direction down towards the recipient G. For obtaining a good function of the apparatus the mixing hose 27 ought to have a larger diameter than the suction hose 19.

Figures 2, 3, 4:
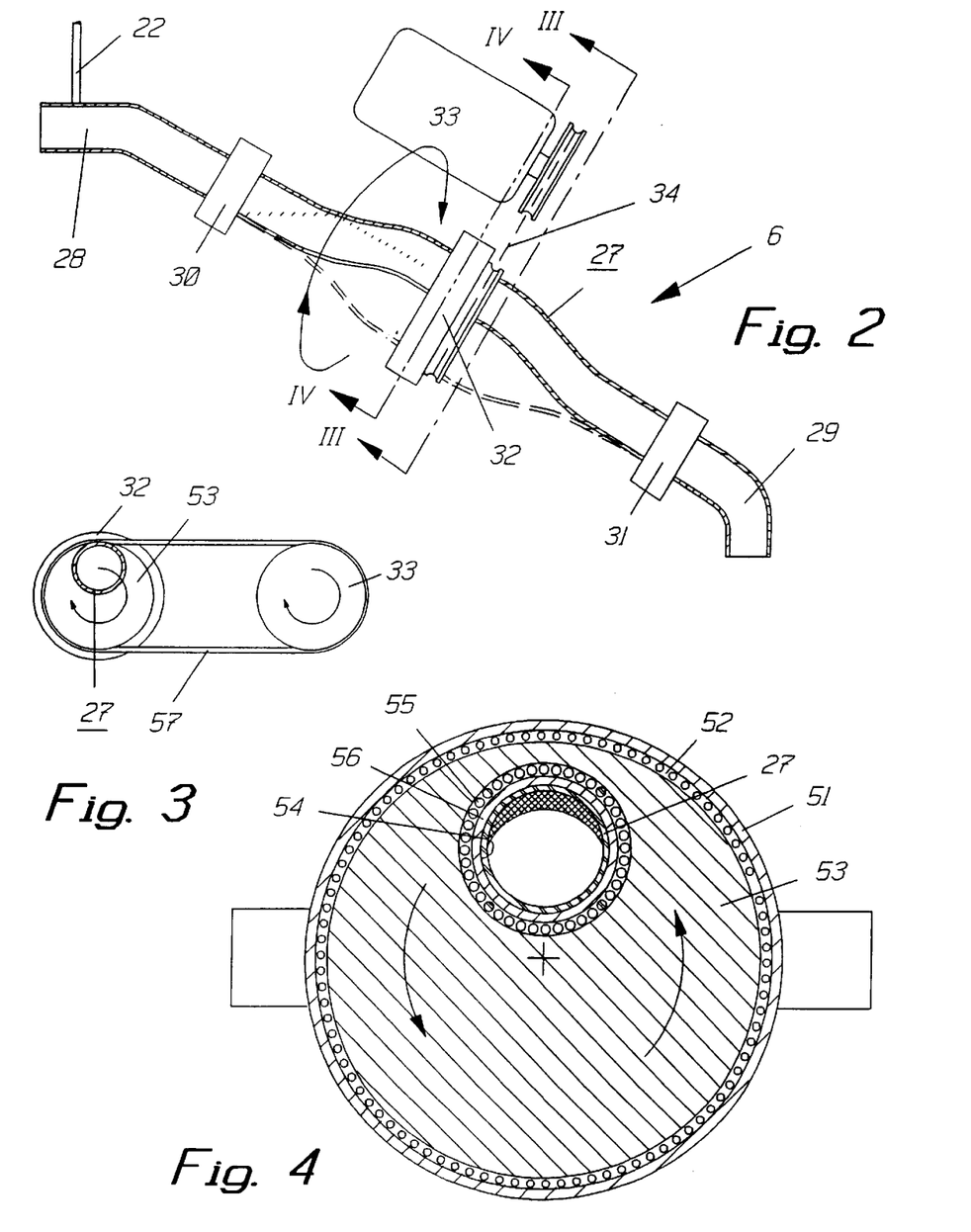
FIG. 2 is an enlarged scale view of a detail of the apparatus of FIG. 1 designed for providing an effective mixing of an additive to the liquid which has been sucked up, and concurrently therewith for providing a de-foaming of the liquid.
FIG. 3 shows a cross section along line III—III of FIG. 2.
FIG. 4 shows, in a still more enlarged scale, a cross section along line IV—IV of FIG. 2.

The mixing and defoaming unit F is shown more in detail in FIGS. 2–4. The unit comprises a flexible hose 27 which is kept stationary between the two hose holders 30, 31 and which by an intermediate part thereof extends through an excentric holder 32 which is best shown in FIG. 4. In the illustrated embodiment the excentric holder comprises a stationary outer ring 51 which rotatably carries an excenter disc 53 over a ball bearing 52. The excenter disc 53 has an exctric bore 54 which, over a ball bearing 55, carries an excenter ring 56 through which the hose 27 extends. The excenter disc 53 and the motor 33 are formed with pulleys for a belt 57 by means of which the motor 33 can rotate the excenter disc 53 together with the hose 27. Thus, the hose 27 is formed with a radially outwards projecting loop providing a centrifugal zone, whereas the hose ends 28, 29 in the holders 30, 31 are rotated about the axial centre of the hose 27.

The Receiver Recipient G

The receiver/collection recipient G comprises a closed container unit 35 at the inner of which the outlet of 29 of the centrifugal hose 27 opens. The container may contain a filter 36 for separating foam which may have been formed when the mixture of liquid and dosing agent is sucked into the container from the mixing unit F, and also a separation filter 37 for separating off particles, bone residuals, eventually existing coagulum etc. A branch conduit 15 opens in the upper part of the container 35, which conduit 15 acts as an evacuation conduit for air which can leave directly through the choke valve B, through the branch conduit 13 and the suction connection 12.

At the bottom of the recipient 35 there is a tapping tube 38 having a tap valve 39. The bottom valve 39 can be of electrically, pneumatically of hydraulically actuatable type, and it cooperates with an upper electrical, optical or capacital level detector 40 which is mounted inside or outside the recipient, and which may be a photocell initiating an opening of the bottom valve 39 when the surface of the liquid reaches said level detector 40, and which closes the valve 39 before the liquid at the bottom of the container 35 is completely emptied. This eliminates the risque that air enters the package bags or the liquid in the packing unit I.

The Packing Unit I

For collecting the blood which has been defoamed, deaerated and filtered there is a collection means I. In the illustrated case the apparatus is, for practical reasons, formed with two liquid containers connected parallelly to each other. The two containers are identical and they are connected to the tapping tube 38 of the recipient 35. Each liquid container comprises a flexible bag 41, 42 which is enclosed in a stiff casing 43, 44. The upper part of each bag 41, 42 is connected to the tapping tube 38 over a branch conduit 45, 46 having a stop valve 47, 48. Each rigid casing 43, 44 is connected to the branch conduit 14 over a stop valve 49, 50 which, when opened and as shown in FIG. 1, places the space between the casing 43 and the bag 41 under the pressure P3 thereby providing a suction action on the bag and a sucking down of liquid from the container 35 when the bottom valve H and any of the valves 47 or 48 is opened. The stiff casing may have a second tube connection with a stop valve arranged for placing the space between the casing and the bag under an over pressure thereby removing any air from the bag, which in the right casing of FIG. 1 is shown in a compressed, air-emptied condition which is the base condition when sucking up liquid.

If desired the packing unit I can be formed so that the liquid of the bag 41 or 42 can be directly introduced into another liquid system, for instance for directly returning to the patient blood which has been treated with citrate, deaerated, filtered and defoamed.

Dosing Unit E'—"outer" System

An embodiment of the "outer" dosing system is shown in FIG. 5. In this case the bag 20' containing the dosing agent, which in case of handling of blood can be a citrate solution, is placed outside the mixing and defoaming unit F, for instande in the open air. In this case the bag 20' containing the dosing agent is under a higher pressure than the pressure P3 in the mixing and defoaming unit F and in the recipient G, for instance atmospheric pressure or a pressure provided by another source, for instance a pressure provided by placing a load 58 on the bag' 20' as indicated with the dotted lines in FIG. 5. The conduit 12 from the source of subpressure means is connected directly to the recipient G. The pressure P3 acts on a liquid column having the height h' between the container bag 20' and the tube inlet end 28 at which the conduit 22' opens. The container bag 20' is mounted on plate which can be raised and lowered and by means of which the height h' of the liquid column can be varied depending on the strength of the pressure P3. Depending on the choking at the tip of the suction nozzle 17 and the length of the suction conduit 19 a substantial pressure gradient P1–P3 is obtained between the pressure of the ambient air (atmospheric) and the pressure of the mixing and the deaeration hose 27 and in the recipient G, respectively.

Adjusting the Dosing Unit E—The "inner" System

The choke valve 23 for the dosing apparatus E is set so that the pressure gradient P2–P3 prevents a flow of liquid dosing agent into the mixing unit F in case only air passes through the suction nozzle 17 and the suction hose 19. The pressure P2 decreases when liquid is sucked into the nozzle 17 and into the suction hose 19 and the pressure gradient decreases towards the value zero, whereby the dosing agent, like citrate, flows from the container 20 which is under the pressure P3, down through the conduit 18 and into the mixing unit F in a predetermined amount in relation to the amount of blood which is sucked through the suction nozzle 17.

It has shown that the relationship between the amount of dosed citrate and the amount of blood which is sucked up is nearly constant irrespective of what amount of blood is sucked up and irrespective of what amount of air is mixed with the blood (the amount of blood foam).

Adjusting the Dosing Unit E'—the "outer" System

The dosing unit is balanced in that the pressure P3 is connected, the suction nozzle 17 is allowed to introduce only air, and the pressure of the container bag 20 and the vertical level of the container bag 20' is adjusted so that the liquid column h' exactly, or nearly exactly reaches as far as to, but not above, the mouth for the dosing tube 22' at the inlet end 28 of the centrifugal hose 27.

This means that no dosing agent is introduced in the centrifugal hose 27 as long as the suction nozzle only sucks air. In such case there is a pressure P3 in the centrifugal hose 27, in the mixing and in the defoaming unit G and as far as at the suction nozzle 17. The subpressure P3 provides a suction force in the mixing and defoaming unit F which balances the liquid column h'.

When a liquid, like blood or blood foam, in sucked up through the suction nozzle 17 the viscosity/flow resistance increases, whereby the pressure P3 is reduced. The reduction of the pressure P3 is proportional to the amount of blood or blood foam which is introduced through the suction nozzle 17. The increasing suction force directly acts on the liquid column h' from the dosing container 20', and dosing agent is sucked into the centrifugal hose 27. The amount of dosing agent which is introduced in the hose 27 thereby is proportional to the amount of blood which is introduced in the system.

Otherwise the "outer" dosing system operates exactly as the "inner" dosing system.

Function of the Apparatus—the "inner" System

The function of the apparatus is as follows:

The suction connection 12 is connected to a source of sub pressure P3, which pressure propagates through the branch conduits 13 and 14 to the dosing apparatus E and to the packing unit I, respectively. From the choke valve B higher pressure P2 propagates to the recipient G and over said recipient also through the mixing and defoaming unit E to the suction nozzle 17, at which a pressure substantially equal to the pressure P2 appears.

As long as only air is introduced through the suction nozzle no additive is supplied, but as soon as liquid enters the suction nozzle 17 dosing agent is automatically added in an amount which is proportional to the amount of liquid entering the suction nozzle 17.

For obtaining a good result in dosing a citrate solution to blood it is preferred to chose the dimensions of the supply tubes 22 of the citration apparatus, and in particular the pressure gradient P2–P3, such that the citration bag 20 issues an amount of citrate corresponding to 8–12% b.w. of the amount of blood entering through the suction nozzle 17 and through the suction hose 19.

The liquid which has been sucked up, in common with the additive which has been dosed into the liquid, is passed to the centrifugal hose 27. Depending on the centrifugal force therein the liquid, or the liquid foam, flowing down the mixing and defoaming unit F towards the radially outwards directed loop 27 is forced radially outwards against the walls of the hose by a successively increased G-force, as indicated with the liquid accumulation in FIG. 4, whereby the dosed liquid additive is effetively mixed with the liquid which has been sucked up by the nozzle, even so that the dosed additive spreads over the entire wall. Concurrently therewith the liquid foam is subjected to such a heavy G-force that the foam bubbles break and the air leaves the foam, and liquid and dosing agent are mixed thoroughly. After having passed the radially outwards directed hose loop the G-force successively decreases so that the liquid mixture, at the end 29 of the hose 27, leaves under a calm flow movement to the collection recipient G.

In the filter 36, 37 of the collection recipient G tissue particles, eventually existing coagulum, muscle particles, bone particles and fat etc. are removed. The air accompanying the liquid into the recipient hereby has the possibility of leaving through the deaeration conduit 15 of the recipient G which is under the higher pressure P2.

When the liquid has reached a predetermined level in the recipient this is observed by the level indicator 40, which may be a photo-cell, and whereby the bottom valve H and any of the valves 47, 48 open, and liquid flows into the container bag 41 or 42 actuated by the sub pressure P3 acting on said bag, and which pressure P3 is less than the pressure P2 in the recipient. The outflow also is initiated by the gravitation force.

When the liquid in the recipient G has reached a certain low level, calculated for preventing introduction of air in the tapping conduit 38 and in the container bag 41 the valve H closes, and a new unit volume is correspondingly built up at the bottom of the recipient.

When the bag in one of the casings, for instance the bag 41 is full, the valves 47 and 49 are closed and the corresponding valves 48 and 50 for the second liquid bag, the right bag 42, are opened whereby said second bag is correspondingly filled with liquid. The content of the full liquid bag 41 can directly be transferred to the patient, eventually via a blood processor. Alternatively said blood bag can be moved to a cool storing means for later use. The full bag 41 in the packing unit I can be emptied by a gravitation flow, but it can alternatively be emptied by applying an over pressure in the chamber between the casing 43 and the bag 41 via some connection means. While operating with a so called heart-lung machine the blood can preferably be directly transferred to the veine reservoir of the machine and from there to the patient.

Function of the Apparatus—the "outer" System

Basically the function of the "outer" system is mainly the same as that of the above described "inner" system. The sub pressure P3 is applied at the suction connection 12, and said sub pressure propagates through the recipient G, through the mixing and defoaming unit F and through the suction hose 19 to the suction nozzle 17. The bottom plate for the citrate bag 20' is adjusted to a height h' of the citrate column at which said column reaches as far as to, but not above, the inlet end 28 of the mixing hose 27 when only air is introduced in the suction hose.

Alternatively the citrate bag 20' is loaded by a weight 58 as indicated with the dotted lines of FIG. 5, and the pressure P3 is set accordingly.

As soon as liquid is introduced through the nozzle 17 the pressure decreases in the connection and recipient system and citrate solution is sucked up through the connection conduit 22' via the one way valve 24', in proportion to the amount of blood that is introduced.

Surface Treatment of Contact Surfaces for Blood

It is known that the contact of blood with foreign materials like the material of the walls of flow passageways and apparatus, like in heart-lung machines etc. may activate the cells and the enzym system of the blood, for instance the coagulation system of the blood, and this strongly influences the quality of the blood in a negative direction. For eliminating said problems while handling of blood by means of the described apparatus it is important that at least the walls of the suction nozzle 17, the suction hose 19 and the mixing hose 27 are made of a blood compatible material which minimizes the activation of the above mentioned system, or are formed with a layer having equivalent properties and which is capable of inhibiting/minimizing the mechanisms which provide the activation of the coagulation system of the blood and which adversely affect the cells of the blood and function thereof. Several methods of providing such layers etc. are known in the art.

| Reference numerals | |
|---|---|
| A suction system | 31 hose holder |
| B choke valve | 32 excenter holder |
| C manometer | 33 motor |
| D suction means | 34 drive belt |
| E dosing unit | 35 container |
| F mixing and defoaming unit | 36 defoaming filter |
| G recipient | 37 separation filter |
| H bottom valve | 38 tapping pipe |
| I packing unit | 39 bottom valve |
| 10 collection container | 40 level indicator |
| 11 emptying means | 41 bag |
| 12 suction connection | 42 bag |
| 13 1:st branch conduit | 43 stiff casing |
| 14 2:nd branch conduit | 44 still casing |
| 15 3:rd branch conduit | 45 branch conduit |
| 16 control means (choke valve) | 46 branch conduit |
| 17 suction nozzle | 47 stop valve |
| 18 nozzle valve | 48 stop valve |
| 19 suction hose | 49 stop valve |
| 20 container | 50 stop valve |
| 21 chamber | 51 outer ring |
| 22 connection conduit | 52 ball bearing |
| 23 stop valve | 53 excenter disc |
| 24 one way valve | 54 bore |
| 25 conduit | 55 ball bearing |
| 26 valve | 56 excenter ring |
| 27 hose | 57 belt disk |
| 28 inlet end (of 27) | 58 load |
| 29 outlet end (of 27) | |
| 30 hose holder | |

We claim:

1. A method for quickly and effectively mixing fluids, each containing at least one liquid phase, with one another comprising the steps of:

aspirating at least one fluid by means of a suction nozzle located at a first end of a suction means, transporting said fluid through said suction means and a mixing and defoaming unit including an inlet end located at a second end of said suction means, dosing a dosing agent into the fluid in said mixing and defoaming unit near said inlet end of said mixing and defoaming unit, from a dosing agent container via a connection conduit, maintaining said dosing agent container under a pressure and controlling the pressure of the dosing agent container such that no dosing agent is supplied to said mixing and defoaming unit when only air is aspirated through the suction means, and whereby dosing agent is supplied to said mixing and defoaming unit when at least one fluid is aspirated through the suction means, the amount of dosing agent supplied being substantially proportional to the amount of the fluid aspirated by said suction means, mixing the aspirated fluid with the dosing agent in the mixing and defoaming unit by virtue of subjecting the fluid and the dosing agent to a G-force other than the force of gravity in said mixing and defoaming unit to thereby provide a quick and effective mixing of the fluid and the dosing agent while eliminating substantially all foam which may be present in the fluid aspirated by the suction means, and collecting the fluid and dosing agent mixture using a calm, laminar flow.

2. A method according to claim 1 wherein said dosing agent is supplied to said mixing and defoaming unit via an internal system formed by the container and a stiff casing which encloses the container, said stiff casing being under a first sub-pressure which is less than a second sub-pressure employed by said suction means to aspirate fluid through said suction means, and balancing said first and second sub-pressures of the inner system such that no dosing agent is supplied when only air is aspirated through the suction means and whereby dosing agent is supplied in an amount substantially proportional to the amount of aspirated fluid when fluid is aspirated by said suction means.

3. A method according to claim 1 wherein said dosing agent is supplied via an outer system from the dosing agent container, said dosing agent container being arranged such that it can be raised and lowered to a position underneath or beside the mixing and defoaming unit and the container being under a pressure which is higher than a pressure present in the mixing and defoaming unit, and balancing the height position of the dosing agent container underneath the mixing and defoaming unit such that no dosing agent is supplied when only air is aspirated through the suction means and whereby dosing agent is supplied as soon as at least one fluid is aspirated through the suction means, said dosing agent being supplied in an amount substantially proportional to the amount of fluid which is aspirated through the suction means.

4. A method as claimed in claim 3 further comprising the step of applying a pressure to the dosing agent container.

5. A method according to claim 1 wherein the G-force is created by flowing the at least one fluid and dosing agent mixture into a hose formed with a radially outwardly directed loop and comprising the step of rotating the hose whereby the fluid and dosing agent mixture is subjected to an increasing G-force while flowing into the radially outwardly directed loop and a decreasing G-force after having passed through said radially outwardly directed loop.

6. A method as claimed in claim 1 wherein the G-force is provided by centrifugation of the at least one fluid and dosing agent mixture.

7. A method according to claim 1 further comprising the step of adjusting the G-force to a value which is optimized for the at least one fluid which has been aspirated by the suction means.

8. An apparatus for performing the method of claim 1 which comprises:

a suction means for aspirating and transporting a fluid containing at least one liquid phase, a dosing means for supplying a dosing agent at a dosing inlet directly into the fluid which is aspirated as soon as any fluid is aspirated by said suction means and in an amount which is substantially proportional to the amount of fluid aspirated by said suction means, mixing and defoaming means for mixing the aspirated liquid with the dosing agent and substantially removing any foam which may be present in the fluid and dosing agent mixture, and wherein the dosing means comprises a container enclosed in a stiff casing, and a means for balancing a first sub-pressure in said container and a second sub-pressure employed to aspirate the at least one fluid through the suction means said first sub-pressure being generally less than said second sub-pressure, and, the mixing and defoaming means applies a G-force other than the force of gravity to said fluid and dosing agent mixture to thereby quickly and effectively mix the fluid and dosing agent and substantially remove any foam which may be present in said fluid.

9. Apparatus according to claim 8 wherein said means for balancing said first and second sub-pressures operates in a manner such that no dosing agent is supplied when only air is aspirated through said suction means, dosing agent is supplied to the aspirated fluid at the inlet of the mixing and defoaming means as soon as at least one fluid is aspirated by the suction means and the amount of dosing agent supplied to said fluid is substantially proportional to the amount of fluid aspirated by said suction means.

10. Apparatus according to claim 9 wherein said mixing and defoaming means comprises a mixing hose having a radially outwardly directed loop and first and second ends of said mixing hose are rotated about a common central axis of said first and second ends to cause said radially outwardly directed loop to act as a centrifuge means whereby the fluid and dosing agent mixture is subjected to an increasing G-force while flowing in said radially outwardly directed loop and a decreasing G-force after passing through said radially outwardly directed loop.

11. Apparatus for performing the method of claim 1 comprising:

a suction means for aspirating and transporting a fluid containing at least one liquid phase, a dosing means for supplying a dosing agent at a dosing inlet directly into the fluid which is aspirated by said suction means in an amount substantially proportional to the amount of fluid aspirated by said suction means, mixing and defoaming means for providing quick and effective mixing of the dosing agent and fluid while substantially removing any foam which may be present in said fluid, wherein said dosing means comprises a dosing agent container which is mounted beneath or beside the dosing inlet such that the dosing agent container can be raised or lowered relative to the dosing inlet, and means for subjecting the dosing agent container to a first sub-pressure which is higher than a second sub-pressure employed to aspirate fluid through the suction means, and wherein the mixing and defoaming means subjects the fluid and dosing agent mixture to a G-force other than the force of gravity such that said fluid and dosing agent mixture is quickly and effectively mixed and at the same time substantially all foam which may be present in said fluid is removed.

12. Apparatus according to claim 11 wherein a dosing conduit is provided between said dosing agent container and said dosing inlet and a combined force of a flow resistance in said dosing conduit and a gravitational force acting on said dosing agent in said dosing conduit is balanced such that no dosing agent is supplied when only air is aspirated through the suction means, whereby dosing agent is supplied to the aspirated fluid via the dosing inlet as soon as fluid is aspirated by the suction means and whereby the amount of dosing agent supplied is substantially proportional to the amount of fluid aspirated by said suction means.

13. Apparatus according to claim 11 wherein the mixing and defoaming unit comprises a mixing hose having a radially outwardly directed loop, and wherein first and second ends of said mixing hose are rotated about a common central axis of said first and second ends whereby said radially outwardly directed loop acts as a centrifuge means such that the fluid and dosing agent mixture is subjected to an increasing G-force while passing through said radially outwardly directed loop and to a decreasing G-force after passing through said radially outwardly directed loop.

* * * * *